(12) United States Patent
Van Dyck

(10) Patent No.: US 6,986,909 B2
(45) Date of Patent: Jan. 17, 2006

(54) SOLID PHASE SYNTHESIS OF SALTS OF ORGANIC ACID

(75) Inventor: Stefaan Van Dyck, Brasschaat (BE)

(73) Assignee: Kemin Industries, Inc., Des Moines, IA (US)

( * ) Notice: Subject to any disclaimer, the term of this patent is extended or adjusted under 35 U.S.C. 154(b) by 389 days.

(21) Appl. No.: 09/918,383

(22) Filed: Jul. 30, 2001

(65) Prior Publication Data

US 2003/0032841 A1 Feb. 13, 2003

(51) Int. Cl.
C07C 55/00 (2006.01)
C07C 51/42 (2006.01)
C07C 59/08 (2006.01)
A23K 1/00 (2006.01)
A23L 1/216 (2006.01)

(52) U.S. Cl. ............. 426/54; 426/96; 562/580; 562/589; 562/590; 562/595; 562/607; 562/609

(58) Field of Classification Search ............ 426/54, 426/96, 74, 428, 606; 562/580, 589, 590, 562/595, 607, 609, 599, 606; 71/11; 549/589, 549/315
See application file for complete search history.

(56) References Cited

U.S. PATENT DOCUMENTS

| | | |
|---|---|---|
| 3,519,571 A | 7/1970 | Szczepanek |
| 3,880,968 A | 4/1975 | Kaspar |
| 3,944,606 A | 3/1976 | Rieger |
| 4,337,722 A | 7/1982 | Debayeux |
| 4,353,709 A | 10/1982 | Nioh |
| 4,700,000 A * | 10/1987 | Merkel et al. ............ 562/606 |
| 4,853,233 A | 8/1989 | McAskie |
| 4,946,654 A | 8/1990 | Uhlemann |
| 4,988,520 A * | 1/1991 | Overton ............ 426/74 |
| 4,996,067 A * | 2/1991 | Kobayashi et al. ........... 426/96 |
| 4,997,469 A * | 3/1991 | Moore ............ 71/11 |
| 5,019,148 A * | 5/1991 | Moore ............ 71/11 |
| 5,045,459 A | 9/1991 | Mothes |
| 5,149,643 A | 9/1992 | Mothes et al. |
| 5,221,673 A | 6/1993 | Budai et al. |
| 5,250,714 A | 10/1993 | Lajoie |
| 5,453,365 A | 9/1995 | Stetzel et al. |
| 5,766,439 A | 6/1998 | Eyal |
| 5,795,615 A | 8/1998 | Nelson et al. |
| 5,935,625 A | 8/1999 | Hornevik et al. |
| 5,935,635 A * | 8/1999 | Mori et al. ............ 426/656 |
| 6,238,709 B1 * | 5/2001 | Kalmbach ............ 426/2 |

FOREIGN PATENT DOCUMENTS

| | | |
|---|---|---|
| CN | 1060580 | 4/1992 |
| CN | 1249301 | 4/2000 |
| CN | 1267661 | 9/2000 |

OTHER PUBLICATIONS

Chemaly Z., Crystallization Kinetics of calcium lactate in a mixed–suspension–mixed–product removal crystallizer. Industrial & Engineering Chemistry Reseach. 38: (7) 2803–2808 Jul., 1999.

Van Halsema, et al. The modeling of carbon dioxide–aided extraction of carboxylic acids from aqueous solutions. Industrial & Engineering Chemistry Research. 37: (3) 748–758 Mar., 1998.

Miller, RW, et al. Extraction of lactic acid from a calcium lactate solution using amine–containing solvents and carbon dioxide gas. Industrial & Engineering Chemistry Research. 35: (4) 1156–1162 Apr., 1996.

* cited by examiner

*Primary Examiner*—Cecilia J. Tsang
*Assistant Examiner*—Taylor Victor Oh
(74) *Attorney, Agent, or Firm*—Kent A. Herink; Daniel A. Rosenberg; Emily E. Harris

(57) ABSTRACT

A process for the solid-phase synthesis of salts of organic acids in a granular, free-flowing, and dust-free form particularly suited for use as animal feed additives. A liquid organic acid is applied to an inert, absorbent carrier. A solid base is then added during stirring. The acid is slowly released from the carrier preventing the fast reactions that lead to the formation of clumps. The exothermic reaction releases heat which assists in reducing the moisture content of the product.

13 Claims, No Drawings

SOLID PHASE SYNTHESIS OF SALTS OF ORGANIC ACID

BACKGROUND OF THE INVENTION

The invention relates generally to the synthesis of salts of organic acids and, more specifically, to the solid phase synthesis of salts of organic acids in a dust-free form particularly suited for use as animal feed additives.

Salts of organic acids are widely used in the animal feed industry as preservatives of the animal feed and as sources of acids in animal feed rations. The salts disassociate in the digestive tract of the animal and provide a number of advantageous effects, including the maintenance of a healthy gastric environment and a beneficial microbial balance. Monogastric animals, such as swine and poultry, must keep a low gastric pH to maintain a healthy gut. Low gastric pH is one of the major factors governing the performance of monogastric animals and the economics of livestock production. The pH of the gut may rise when the animals are young or under stress. The addition of salts of organic acids to the animal feed ration helps to lower the gastric pH and improve the health of the animal.

A satisfactory animal feed acidifier product must function as an acidifier, blend with the animal feed ration, be acceptable to the animal, and not grossly alter the physical characteristics of the animal feed. Problems have occurred in the production of animal feed acidifiers in the form of clumping of the acidifier during manufacture, requiring an additional processing step to comminute the acidifier to a size where it can be blended with the animal feed ration, be acceptable to the animal, and provide a bioavailable source of the organic acid upon ingestion. Comminution of clumps can result in the production of fines, i.e., finely divided particles that create dustiness, resulting in a loss of product during mixing into the animal feed ration and an unpleasant environment for persons conducting the mixing. Other methods of producing these products have required an additional energy-consuming step to remove excess water, such as distillation or spray drying. There is needed a method of producing salts of organic acids that results in a feed acidifier that has a small particle size without the presence of fines, which does not clump during formation and which does not require additional drying.

Animal feed acidifiers are commonly added to animal rations that also include mineral premixes. Many of the mineral premixes include either or both amino acids and copper sulfate. These ingredients react with the volatile acids of the animal feed acidifier to form clumps. There is a need for a method of producing salts of organic acids that does not cause clumping when combined with mineral premixes including either amino acids or copper sulfate.

SUMMARY OF THE INVENTION

The invention consists of a method of synthesizing salts of organic acids using solid phase synthesis. The liquid organic acid is added to an acceptable, inert carrier. A solid base is added during mixing. The acid is slowly released from the carrier preventing the fast reactions that lead to the formation of clumps. The exothermic reaction releases heat which assists in reducing the moisture content of the product. The process can be repeated to increase the loading of the salt on the carrier. The resulting product is comprised of free-flowing granules. The average particle size increases slightly with the number of repetitions of adding the acid and base to the carrier. A loading of between about 65% and 80% of the organic acid salt on the carrier can be easily achieved, depending in part on the characteristics of the organic acid being used, without undue clumping of the product.

An object of the invention is to provide a method of synthesizing salts of an organic acid in form that is free-flowing and of a small particle size relatively free of dust, particularly suited for use as an animal feed acidifier.

Another object of the invention is to provide a method of synthesizing salts of an organic acid that is adaptable to adjust the loading of the organic salt on an inert carrier.

These and other objects of the invention will be made apparent to those skilled in the art upon a review of this specification and the appended claims.

DETAILED DESCRIPTION OF PREFERRED EMBODIMENTS

The method generally comprises the addition of a liquid organic acid to an inert carrier in an amount sufficient to moisten the carrier. A dry base is slowly added to the moistened carrier during mixing. The base reacts with the acid as it is relatively slowly released from the carrier. The slow release of the acid prevents the fast reaction that can lead to clumping. Additionally, the heat released during the exothermic reaction between the acid and base assists in reducing the moisture content of the mixture. If desired, once the moisture content of the mixture has been reduced, additional liquid acid can be added to the mixture, followed by the adding of additional base, in order to increase the loading of the organic salt on the carrier.

Organic acids suitable for use in the present process are all liquid organic acids. Preferred organic acids include lactic acid, propionic acid, acetic acid, butyric acid, and formic acid and mixtures thereof. Bases suitable for use in the present process include alkali metal hydroxides and alkaline-earth metal bases, including calcium oxide, calcium hydroxide, sodium hydroxide and potassium hydroxide and mixtures thereof. Carbonates, such as calcium carbonate, sodium carbonate, and sodium bicarbonate, cannot be used as the sole bases in the reaction because of the formation of carbon dioxide during the reaction with the acids and because the reaction is not sufficiently exothermic to complete drying of the product. These bases may be used, however, in combination with the preferred bases.

During the first loading of the carrier with the liquid acid, it is preferable to avoid excess wetting of the carrier. A preferred range of the weight ratio of carrier to acid is between about 1:1 and 3:1, and more preferably, between about 1.5:1 and 2:1, giving consideration to the water content of the acid being used. For example, using lactic acid (80% feed grade), a ratio of 2:1 can be used, whereas when using propionic acid, a ratio of 1.5:1 is the preferred maximum.

The total loading of the carrier can be increased by repeated cycles of adding acid and base to the carrier. The maximum preferred loading that can be obtained is dependent on the acid. For lactic acid (80% feed grade), a preferred product is obtained until the product contains about 65% calcium lactate and 35% carrier. Further loading of the salt on the carrier makes the product more difficult to process as it becomes sticky. Also, the size profile of the granules of the product changes as the loading is increased above a certain level. Above about 65%, granules in the range of 0.5 to 1 cm appear, with a fraction even larger. For propionic acid, a preferred product is obtained until the product contains about 80% calcium propionate and 20% carrier. Further loading, while presenting no processing difficulties, begins to result in increased dustiness. This may be because the newly produced salt is no longer in contact with the carrier. Dustiness can be reduced, even at a loading above 80%, by the addition of a small amount of feed grade lactic acid.

Additional free acids in their solid form, such as fumaric or ascorbic acid, can be incorporated into the product after the last salt formation reaction. The free acids are preferably added when the temperature of the mixture is observed to start to drop. The acids are thus incorporated into the granules of the product during the drying process. In the same way, other powdered or granular materials can be incorporated into the product, such as mineral salts, minerals, antioxidants, or amino acids. A loading of up to about 50% of such additional ingredients can usually be obtained with the ingredient being incorporated into the product granules. Additional loading of the added ingredients can be made, but not all of the added ingredient may be incorporated into the granules.

EXAMPLE 1

Solid Phase Synthesis of Calcium Lactate

Feed grade (80%) lactic acid in the amount of 35 g is divided into three equal fractions. Calcium hydroxide, 10.153 g, and 0.946 g of calcium oxide are combined, mixed, and divided into three equal fractions. The first fraction of lactic acid is added to 20 g of almond shell meal while stirring. Then, the first fraction of the combined base mixture is slowly added while stirring. The temperature of the mixture is observed to increase and water starts evaporating. When the product appeared to be dry, the same procedure was repeated for the remaining fractions, adding the acid while stirring, adding the base while stirring and drying. The reaction heat can be modified by adjusting the ratio of calcium oxide to calcium hydroxide.

EXPERIMENT 2

Use of other Carriers

Experiment 1 was repeated using as alternatives to almond shell meal 20 g of palm kernel meal, cacao meal, silica gel, and sand as the carrier. Palm kernel meal and cacao meal produced a suitable product similar to the almond shell meal albeit that the particle size was more variable. Silica gel carrier resulted in a product with much smaller particle size. Sand was not suitable; it is believed that being non-porous it did not absorb the acid.

EXPERIMENT 3

Solid Phase Synthesis of Calcium Propionate

Propionic acid in the amount of 30 g is divided into three equal fractions. Calcium hydroxide, 10.153 g, and 0.946 g of calcium oxide are combined, mixed, and divided into three equal fractions. The first fraction of propionic acid is added to 20 g of almond shell meal while stirring. Then, the first fraction of the combined base mixture is slowly added while stirring. The temperature of the mixture is observed to increase and water starts evaporating. When the product appeared to be dry, the same procedure was repeated for the remaining fractions, adding the acid while stirring, adding the base while stirring and drying.

The heat of reaction was high, causing the product to dry quickly. Medium sized porous lumps were formed which could be easily broken by hand. An alternative formulation was developed to attempt to reduce the heat of the reaction, either by replacing the calcium oxide with an equimolar amount of calcium hydroxide or diluting the acid with water.

The experiment was repeated using 30 g of 80% propionic acid, 10.81 g of calcium hydroxide and 0.91 g or calcium oxide. A non-dusty product without lumps was formed.

EXPERIMENT 4

Solid Phase Synthesis of a Mixture of Salts

Twenty-one grams of lactic acid (food grade=80%) and 9 g propionic acid were combined and divided into three equal fractions. Calcium hydroxide, 10.256 g, and 0.862 g of calcium oxide are combined, mixed, and divided into three equal fractions. The first fraction of the acid combination is added to 20 g of almond shell meal while stirring. Then, the first fraction of the combined base mixture is slowly added while stirring. The temperature of the mixture is observed to increase and water starts evaporating. When the product appeared to be dry, the same procedure was repeated for the remaining fractions, adding the acid while stirring, adding the base while stirring and drying.

This method produced a non-dusty granulated product.

In an alternative experiment, a small amount (approx. 1 cm$^3$) of butyric acid was added to the acid mixture before dividing. A similar product resulted.

EXAMPLE 5

Scaled-Up Solid Phase Synthesis of Calcium Lactate

Food grade (80%) lactic acid in the amount of 14.4 kg is divided into three equal fractions. Calcium hydroxide, 4.2 kg, and 0.39 kg of calcium oxide are combined, mixed, and divided into three equal fractions. The first fraction of lactic acid is added to 9.8 kg of almond shell meal while stirring. Then, the first fraction of the combined base mixture is slowly added while stirring. The temperature of the mixture is observed to increase and water starts evaporating. When the product appeared to be dry, the same procedure was repeated for the remaining fractions, adding the acid while stirring, adding the base while stirring and drying.

A non-dusty granulated product was obtained with a yield of 26 kg.

EXAMPLE 6

Solid Phase Synthesis of Calcium Propionate with a Higher Loading of Carrier

An experiment was conducted to see the effect of higher loading of the organic acid salts on the carrier by increasing the number of times the acid and base amounts were added to the carrier. In each step, 10 g or propionic acid (80%), and 3.603 g. of calcium hydroxide combined with 0.303 g of calcium oxide were applied to 20 g of almond shell meal as described above. The temperature of the mixture is observed to increase and water starts evaporating. When the product appeared to be dry, the same procedure was repeated, adding the acid while stirring, adding the base while stirring and drying.

A non-dusty granulated product resulted through 5 additions of the acid. By repeated additions of acid and base, a ratio of 9:1 salt:carrier can be reached although the dustiness of the product increases. It was found that adding 10% lactic acid (feed grade 80%) to the propionic acid significantly reduced the dustiness of the product.

EXAMPLE 7

Solid Phase Synthesis of a Mixture of Salts, Including Calcium Lactate

Feed grade (80%) lactic acid in the amount of 16.56 g is combined with 24.86 g propionic acid and divided into three equal fractions. Calcium hydroxide, 16.81 g, is divided into three equal fractions. The first fraction of lactic acid is added to 20 g of almond shell meal while stirring. Then, the first fraction of the combined base mixture is slowly added while stirring. The temperature of the mixture is observed to increase and water starts evaporating. When the product appeared to be dry, the same procedure was repeated for the remaining fractions, adding the acid while stirring, adding the base while stirring and drying. After the addition of the last fraction of the base, the evaporation of water from the mixture is closely observed. As soon as the rate of evaporation is observed to decrease, the fumaric acid is added while stirring. Because the produced salt is not yet dry, the fumaric acid agglomerates with the salt, yielding a granule comprising an organic salt and a free organic acid.

A non-dusty product is obtained. This experiment shows that it is possible to incorporate other chemicals with the organic salt product. In this experiment, calcium oxide was omitted to slow down the drying process. Another approach would be to keep the calcium oxide but dilute the acid.

EXPERIMENT 8

Quantification of the Effect of Calcium Oxide on the Reaction Temperature

To evaluate the effect of the addition of calcium oxide on the heat of the reaction and thus the drying process, the temperature of the reaction mixture was measured for the reaction of 30 g almond shell meal, 10 g propionic acid (80%), and 4.00 g calcium hydroxide. The maximum temperature reached by the reaction mixture was 60.7° C. Subsequently, the temperature of the reaction mixture was measured for the reaction of 30 g almond shell meal, 10 g propionic acid (80%), and 3.03 g calcium oxide. The maximum temperature reached by the reaction mixture was 70.7° C.

This experiment demonstrates the beneficial effect of the calcium oxide addition for the exothermic removal of water during the process and its consumption of an equimolar amount of water in the chemical reaction of CaO with water. This also indicates that the calcium oxide/calcium hydroxide ratio can be used to optimise the drying process.

EXPERIMENT 9

Particle Size Distribution

The distribution in particle size was measured following the reaction of propionic acid and calcium hydroxide/calcium oxide without the use of a carrier. The results are presented in Table 1.

TABLE 1

| Particle size | % |
|---|---|
| >3.15 mm | 0 |
| 3.15–2 mm | 1.7 |
| 2–1 mm | 5.6 |
| 1–0.85 mm | 3.3 |
| 0.85–0.425 mm | 12.4 |
| <0.425 mm | 77.0 |

The particle size distribution of almond shell meal prior to loading with the organic acid salt is presented in Table 2.

TABLE 2

| Particle size | % |
|---|---|
| >3.15 mm | 0 |
| 3.15–2 mm | 0 |
| 2–1 mm | 0 |
| 1–0.85 mm | 0 |
| 0.85–0.425 mm | 25.8 |
| <0.425 mm | 74.2 |

The particle size distribution of almond shell meal (20 g) after one, two, and three loadings with calcium propionate (each loading is produced using 10 g propionic acid, 4.392 g calcium hydroxide/0.488 g calcium oxide) is presented in Table 3.

TABLE 3

| Particle size | First Loading % | Second Loading % | Third Loading % |
|---|---|---|---|
| >3.15 mm | 0 | 0.5 | 1.0 |
| 3.15–2 mm | 0.1 | 2.0 | 2.4 |
| 2–1 mm | 7.8 | 13.4 | 10.5 |
| 1–0.85 mm | 9.2 | 8.9 | 7.5 |
| 0.85–0.425 mm | 66.2 | 57.3 | 57.0 |
| <0.425 mm | 15.7 | 17.9 | 21.76 |

The particle size distribution of almond shell meal (20 g) after one, two, and three loadings with calcium lactate (each loading is produced using 10 g 80% feed grade lactic acid, 2.889 g calcium hydroxide/0.321 g calcium oxide) is presented in Table 4.

TABLE 4

| Particle size | First Loading % | Second Loading % | Third Loading % |
|---|---|---|---|
| >3.15 mm | 0 | 4.9 | 1.2 |
| 3.15–2 mm | 0 | 19.3 | 11.4 |
| 2–1 mm | 5.9 | 56.8 | 63.5 |
| 1–0.85 mm | 15.4 | 7.5 | 9.0 |
| 0.85–0.425 mm | 71.6 | 10.4 | 14.4 |
| <0.425 mm | 7.1 | 1.1 | 0.5 |

The particle size distribution of almond shell meal (20 g) after one, two, and three loadings with calcium lactate/calcium propionate mixture (each loading is produced using 1 g 80% feed grade lactic acid and 9 g propionic acid, 4.239 g calcium hydroxide/0.471 g calcium oxide) is presented in Table 5.

TABLE 5

| Particle size | First Loading % | Second Loading % | Third Loading % |
|---|---|---|---|
| >3.15 mm | 0 | 4.4 | 2.8 |
| 3.15–2 mm | 3.4 | 1.0 | 4.0 |

TABLE 5-continued

| Particle size | First Loading % | Second Loading % | Third Loading % |
|---|---|---|---|
| 2–1 mm | 5.1 | 9.4 | 19.0 |
| 1–0.85 mm | 4.5 | 7.4 | 11.3 |
| 0.85–0.425 mm | 56.6 | 58.7 | 49.8 |
| <0.425 mm | 33.4 | 23.1 | 13.1 |

When these results are compared with the particle size distribution of the pure calcium propionate on the carrier it is clear that the calcium propionate becomes more dusty after each loading step (although still a lot less dusty than the propionate without a carrier). For the lactate/propionate mixture, a decrease of the dustiness is observed for each additional loading, particularly the amount of the smallest particles (<0.425 mm) which are an important contributor to dustiness.

EXPERIMENT 10

Alternative Bases

The use of alternative bases, such as alkali metal bases and organic bases, was investigated. Sodium hydroxide and potassium hydroxide are hygroscopic and are therefore typically sold in pelleted form. For use in the present method, the pellets of these bases are freshly ground and then used immediately in the synthesis.

To 20 g of almond meal, 10 g of propionic acid is added while stirring. Then, 7.57 g of freshly ground KOH is added while stirring. The stirring is stopped when the temperature of the reaction mixture drops below 30° C. Further loading of the carrier can be accomplished by repeated cycles of adding acid and base. Preferably, approximately 7 g of additional carrier is added to shorten the drying time. After the final loading, the mixture is stirred until the desired dryness is obtained. If loading above 70% is attempted, drying time increases to more than 30 minutes.

To 10 g of almond shell meal, 2.64 g of propionic acid is added while stirring. Thereafter, 5 g of a 25% ammonium hydroxide solution is added while stirring. When the temperature of the reaction mixture drops below 40° C., an additional 20 g of almond shell meal is added. Next, 5.28 g of propionic acid is mixed with the carrier followed by the addition of 4.0 g of calcium oxide while stirring. Alternating steps of ammonium propionate and calcium propionate synthesis can follow by repeating these steps.

EXPERIMENT 11

Use of Diluted Acids and Diluted Bases

It is possible to use more diluted acids for the production of calcium salts by using only calcium oxide as the base. The maximum water content of the acids was determined by performing the reaction with 100% calcium oxide. It was found that lactic acid diluted to 60% could be used to obtain a loading of up to 65% on to the carrier. It was found that propionic acid diluted to 70% could be used to obtain a loading of up to 80% on to the carrier.

Diluted bases can be used if they are combined with an additional step that aids in the drying. This can be accomplished by the addition of silica gel or a combination with another exothermic salt formation reaction. In this experiment, 6.94 g of propionic acid is added to 30 g or almond shell meal while stirring. Then 7.5 g of 50% NaOH is added while stirring. When the mixture has cooled to 30° C., 3 g of silica gel are added. This procedure is repeated, with a maximal loading of the salt on to the carrier of 50%. It should be noted that the addition of silica gel adds to the dustiness of the product.

EXPERIMENT 12

Inclusion of Additional Compounds

The method also may be practiced wherein other ingredients or compounds are incorporated into the granulate. Examples of such ingredients are solid organic acids (e.g., citric acid, ascorbic acid, and fumaric acid), mineral salt solutions (e.g., copper sulfate), natural or synthetic surfactants, flavorings, colorants, and pigments. In a specific example, to 30 g of almond shell meal, 15 g or a diluted solution of one of the foregoing additional ingredients is added while stirring. Thereafter, 10 g or the organic acid is added, followed by and equivalent amount of the selected base, all while stirring. When the temperature of the mixture drops below 35° C., the procedure is repeated twice more.

The foregoing description comprise illustrative embodiments of the present inventions. The foregoing embodiments and the methods described herein may vary based on the ability, experience, and preference of those skilled in the art. Merely listing the steps of the method in a certain order does not necessarily constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

What is claim is:

1. A process for the preparation of a granular organic acid salt animal feed supplement, comprising the steps of:
   (a) combining in a reaction vessel an inert carrier; and a liquid organic acid which is absorbed by the carrier;
   (b) adding to the reaction vessel an inorganic base which reacts with the organic acid in an exothermic reaction to produce a granular organic acid salt animal feed supplement; and
   (c) allowing the organic acid salt animal feed supplement to dry without the use of additional sources of heat.

2. A process as defined in claim 1, further comprising the step of repeating the steps of adding the organic acid and adding the base.

3. A process as defined in claim 1, wherein the carrier is selected from the group consisting of a plant material, silica gel, and combinations of the plant material and silica gel.

4. A process as defined in claim 1, wherein the organic acid is selected from the group consisting of acetic, ascorbic, citric, formic, fumaric, lactic, and propionic acids.

5. A process as defined in claim 1, wherein the base is selected from the group consisting of alkali metal hydroxides.

6. A process as defined in claim 1, wherein the base is selected from the group consisting of alkaline-earth metal bases.

7. A process as defined in claim 6, wherein the alkaline-earth metal bases are selected from the group consisting of oxides of alkaline-earth metals.

8. A process as defined in claim 7, wherein the oxides of alkaline-earth metals are selected from the group consisting of calcium hydroxide and calcium oxide.

9. A process as defined in claim 1, wherein the weight ratio of carrier to organic acid is in the range of between about 1:1 and about 3:1.

10. A process as defined in claim 1, wherein the amount of base used is sufficient to react with the amount of acid.

11. A process as defined in claim 1, wherein the steps are repeated until the weight ratio of organic salt to carrier is in the range of between about 1.5:1 and about 4:1.

12. A process for the preparation of a granular organic acid salt animal feed supplement, comprising the steps of:

(a) combining in a reaction vessel an inert carrier and a liquid organic acid which is absorbed by the carrier;

(b) and then adding to the reaction vessel an organic base, selected from the group consisting of alkali metal bases and alkaline-earth metal bases, which reacts with the organic acid in an exothermic reaction to produce a granular organic acid salt animal feed supplement; and (c) allowing the organic acid salt animal feed supplement to dry without the use of additional sources of heat.

13. A method as defined in claim 12, wherein the weight ratio of carrier to organic acid is in the range of between about 1:1 and about 3:1.

\* \* \* \* \*